(12) United States Patent
Phillips et al.

(10) Patent No.: US 6,403,628 B1
(45) Date of Patent: Jun. 11, 2002

(54) PESTICIDAL 1-ARYLPYRAZOLES

(75) Inventors: Jennifer Phillips, Apex; Michael Pilato, Cary; Tai-Teh Wu, Chapel Hill, all of NC (US)

(73) Assignee: Rhone-Poulenc Agro, Lyons (FR)

( * ) Notice: Subject to any disclaimer, the term of this patent is extended or adjusted under 35 U.S.C. 154(b) by 0 days.

(21) Appl. No.: 09/578,859

(22) Filed: May 26, 2000

Related U.S. Application Data

(62) Division of application No. 09/339,175, filed on Jun. 24, 1999, now Pat. No. 6,087,387, which is a continuation of application No. PCT/EP97/07115, filed on Dec. 18, 1997.
(60) Provisional application No. 60/033,887, filed on Dec. 24, 1996.

(51) Int. Cl.$^7$ .................. A01N 43/50; C07D 231/44
(52) U.S. Cl. ................... 514/404; 548/367.4
(58) Field of Search ................ 548/367.4; 514/404

(56) References Cited

U.S. PATENT DOCUMENTS

| | | | |
|---|---|---|---|
| 4,804,675 A | 2/1989 | Jensen-Korte et al. | |
| 4,918,085 A | 4/1990 | D'Silva et al. | |
| 5,047,550 A | 9/1991 | D'Silva | |
| 5,232,940 A | 8/1993 | Hatton et al. | |
| 5,451,598 A | 9/1995 | Salmon | |
| 5,580,843 A | 12/1996 | Stetter et al. | |
| 6,087,387 A | 7/2000 | Phillips et al. | |

FOREIGN PATENT DOCUMENTS

| | | |
|---|---|---|
| DE | 19511269 | 10/1995 |
| DE | 19518054 | 9/1996 |
| EP | 0201852 | 11/1986 |
| EP | 0295117 | 12/1988 |
| EP | 0412849 | 2/1991 |
| EP | 0511845 | 11/1992 |
| EP | 0659745 | 6/1995 |
| EP | 0679650 | 11/1995 |
| EP | 0780378 | 6/1997 |
| EP | 0822187 | 2/1998 |
| WO | 87/03781 | 7/1987 |
| WO | 93/06089 | 4/1993 |
| WO | 94/21606 | 9/1994 |
| WO | 96/24589 | 8/1996 |

*Primary Examiner*—Robert W. Ramsuer
(74) *Attorney, Agent, or Firm*—Burns, Doane, Swecker & Mathis, L.L.P.

(57) ABSTRACT

The invention relates to 1-phenylpyrazole derivatives of formula (I):

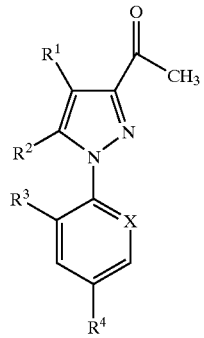

wherein $R^1$, $R^2$, $R^3$, $R^4$ and X are as defined in the description, and to their use as insecticides.

18 Claims, No Drawings

PESTICIDAL 1-ARYLPYRAZOLES

CROSS-REFERENCE TO RELATED APPLICATIONS

This application is a division of U.S. patent application Ser. No. 09/339,175, filed Jun. 24, 1999, U.S. Pat. No. 6,087,387, incorporated by reference herein in its entirety and relied upon, which is a continuation of International Patent Application No. PCT/EP97/07115, filed Dec. 18, 1997 and designating the United States, which is incorporated by reference herein in its entirety and relied upon, and which claims the priority of U.S. Provisional Patent Application No. 60/033,887, filed Dec. 24, 1996.

BACKGROUND OF THE INVENTION

1. Field of the Invention

This invention relates to 3-acetyl-1-aryl-pyrazole derivatives useful in the control of insects, nematodes or helminths, and to compositions containing the same. The method of the invention particularly relates to the application of the 1-arylpyrazole derivatives under conditions where some worker exposure is likely to occur. The invention also relates to a new and improved method of control of insects, nematodes or helminths, using an insecticidally active material having a 1-phenyl pyrazole group therein and is particularly useful for the control of aphids.

2. Description of the Related Art

The control of insects, nematodes or helminths by means of active material having a 1-arylpyrazole group therein has been described by many patents or patent applications such as International Patent Publication No. WO 93/06089 (and the equivalent U.S. Pat. No. 5,451,598), WO 94/21606 and WO 87/03781 as well as in European Patent Publication Numbers 0295117, 659745, 679650, 201852 and 412849, German Patent No. DE19511269 and U.S. Pat. No. 5,232,940.

The first object of the instant invention is to provide an improved level of safety to the user and the environment in the methods of control of insects, nematodes or helminths. All pesticides are generally more or less hazardous, and it is always desirable to lower the potential hazards which might exist even if these are quite low and acceptable for normal uses. Thus it is an object of the instant invention to develop a method of control wherein the potential hazards are lowered by comparison with the known and existing methods, even if these existing hazards are low and acceptable.

A second object of the invention is to lower the hazards for working people in such methods of use. A third object of the present invention is to lower the hazards for working people in such methods of use when a substantial exposure might occur.

A fourth object of the present invention is to provide a new and better method of control of aphids. The control of aphids by many insecticidally active materials is known but these insect species are capable of extremely rapid population growth with a substantial and higher risk of resistance developing to pesticides than occurs for other insect species. Thus it is highly desirable to be able to introduce new methods of control using pesticides other than those used up to now. It is an object of the instant invention to provide a method of control using insecticidally active material of the 1-phenyl pyrazole type which has a high efficiency, and if possible, a better efficiency than the methods known up to now.

A fifth object of the present invention is to provide new 1-phenylpyrazole derivatives which possess improved systemic aphicidal activity compared to known compounds. These compounds possess excellent properties in controlling cotton leaf aphid (*Aphis gossypii*) and greenbug (*Schizaphis graminum*) in systemic applications.

These and other objects of the invention shall become readily apparent from the description of the present invention which follows, and are achieved in whole or in part by the invention.

SUMMARY OF THE INVENTION

This invention provides an improvement in a method of control of insects by means of application of an insecticidally active ingredient having a 1-arylpyrazole group to a locus where insects are present or expected to be present, said application being made under conditions whereby an exposure of mammalian species, especially a substantial exposure, may occur, the improvement whereby the said active ingredient has a 3-acetyl substituent on the pyrazole ring. The method of control of the invention is particularly suitable when there may be an exposure to working people.

The invention also provides a method of control of insects by means of application of an insecticidally active ingredient having a 1-arylpyrazole group to a locus where aphids insects are present or expected to be present, the improvement whereby the said active ingredient has a 3-acetyl substituent on the pyrazole ring.

Practically the applications according to the inventions are using an active ingredient of formula (I):

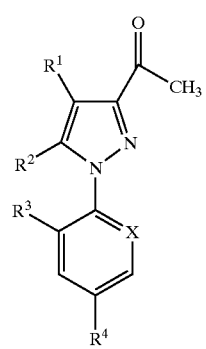

(I)

wherein:

$R^1$ is $S(O)_m R^5$;

$R^2$ is selected from a hydrogen atom, a halogen atom —$NR^6 R^7$, —$S(O)_n R^8$, $C(O)R^8$, $C(O)OR^9$, alkyl, haloalkyl, —$OR^9$, or —$N=C(R^{10})(R^{11})$;

$R^3$ is selected from a halogen atom or the hydrogen atom;

$R^4$ is selected from a halogen atom, haloalkyl, haloalkoxy, —$S(O)_p CF_3$, or —$SF_5$;

$R^5$ is alkyl or haloalkyl;

$R^6$ and $R^7$ are independently selected from a hydrogen atom, alkyl, haloalkyl, —$C(O)$ $R^8$, $C(O)OR^8$, —$S(O)_q CF_3$; the alkyl portions of which are optionally substituted by one or more $R^{12}$; or $R^6$ and $R^7$ are joined so as together form a divalent radical having 4 to 6 atoms in the chain, this divalent radical being alkylene, alkyleneoxyalkylene or alkyleneaminoalkylene, preferably to form a morpholine, pyrrolidine, piperidine or piperazine ring;

$R^8$ is alkyl or haloalkyl;

$R^9$ is selected from alkyl, haloalkyl or the hydrogen atom;

$R^{10}$ is selected from $R^9$ or alkoxy;

$R^{11}$ is alkyl or haloalkyl; or is selected from phenyl or heteroaryl that is optionally substituted by one or more groups selected from hydroxy, halogen, alkoxy, —S(O)$_r$R$^8$, cyano, $R^8$ or combinations thereof;

$R^{12}$ is selected from cyano, nitro, alkoxy, haloalkoxy, —S(O)$_s$-alkyl, —S(O)$_s$-haloalkyl, C(O)-alkyl, C(O)-haloalkyl, C(O)O-alkyl, C(O)O-haloalkyl, aminocarbonyl, alkylaminocarbonyl, dialkylaminocarbonyl, hydroxy, aminosulfonyl, alkylaminosulfonyl or dialkylaminosulfonyl;

X is selected from the nitrogen atom, or the radical C—$R^{13}$;

$R^{13}$ is a halogen atom; and m, n, p, q, r and s represent, independently of one another, the values zero, one or two;

or a pesticidally acceptable salt thereof.

By the term "pesticidally acceptable salts" is meant salts the anions and cations of which are known and accepted in the art for the formation of pesticidally acceptable salts. Preferably such salts are water soluble. Suitable acid addition salts formed from compounds of formula (I) containing an amine group, include salts with inorganic acids for example hydrochlorides, phosphates, sulfates and nitrates, and salts with organic acids for example acetates. Suitable salts formed with bases from compounds of formula (I) containing a carboxylic acid group, include alkali metal (for example sodium or potassium) salts, ammonium salts and organic amine (for example diethanolamine or morpholine) salts.

DETAILED DESCRIPTION OF THE INVENTION

Unless otherwise specified alkyl and alkoxy groups have from one to four carbon atoms. The haloalkyl and haloalkoxy groups likewise preferably have one to four carbon atoms. The various individual aliphatic hydrocarbon moieties, that is, radicals and portions thereof (for example the alkyl moiety of alkylaminocarbonyl and alkylaminosulfonyl) have up to four carbon atoms in the chain.

The haloalkyl and haloalkoxy groups can bear one or more halogen atoms.

The term heteroaryl refers to a five to seven membered heterocyclic ring containing from one to four heteroatoms selected from nitrogen, oxygen and sulfur.

The term halogen means F, Cl, Br or I. The term "halo" before the name of a radical means that this radical is partially or completely halogenated, that is to say, substituted by F, Cl, Br or I, in any combination, preferably by F or Cl.

$R^2$ is preferably an amino group, which is unsubstituted or which bears one or two substituents selected from the group consisting of alkyl, —C(O) $R^8$ and —C(O)OR$^8$; the alkyl portions of which are optionally substituted by one or more $R^{12}$.

$R^3$ is preferably a halogen atom; especially preferred is a chlorine atom; $R^4$ is preferably selected from a halogen atom, haloalkyl, haloalkoxy, or —SF$_5$; especially preferred are CF$_3$—, CF$_3$O— and —SF$_5$.

$R^5$ is preferably methyl, ethyl or propyl.

A particularly preferred group of compounds of general formula (I) because of their systemic aphicidal properties are those wherein:

$R^2$ is NR$^6$R$^7$;

$R^3$ is halogen;

$R^4$ is CF$_3$—, CF$_3$O— or —SF$_5$;

$R^5$ is alkyl;

X is CR$^{13}$;

$R^{13}$ is halogen; and m is 0 or 1.

A further particularly preferred class of compounds of general formula (I) because of their systemic aphicidal properties are those wherein:

$R^2$ is NR$^6$R$^7$;

$R^3$ is chlorine;

$R^4$ is CF$_3$—, CF$_3$O— or —SF$_5$;

$R^5$ is alkyl;

$R^6$ is hydrogen;

$R^7$ is hydrogen, —S(O)$_q$CF$_3$, or alkyl optionally substituted by —S(O)$_s$R$^8$ or aminocarbonyl;

X is CR$^{13}$;

$R^{13}$ is chlorine or bromine; and m is 0 or 1.

A further particularly preferred class of compounds of general formula (I) because of their systemic aphicidal properties are those wherein:

$R^2$ is NR$^6$R$^7$;

$R^3$ is chlorine;

$R^4$ is CF$_3$— or —SF$_5$;

$R^5$ is methyl or ethyl;

$R^6$ is hydrogen;

$R^7$ is hydrogen, methyl or ethyl optionally substituted by —S(O)$_s$R$^8$ or aminocarbonyl;

$R^8$ is methyl or ethyl;

$R^9$ is methyl or ethyl;

X is CR$^{13}$;

$R^{13}$ is chlorine or bromine; and m is 0 or 1.

Particularly preferred pyrazole derivatives usable in the method for control of insects within the scope of the present invention include the following. The numbers 1–12 are assigned to these compounds for reference and identification.

1. 3-acetyl-5-amino-1-(2,6-dichloro-4-trifluoromethylphenyl)-4-methylsulfinylpyrazole
2. 3-acetyl-5-amino-1-(2,6-dichloro-4-trifluoromethylphenyl)-4-methylthiopyrazole
3. 3-acetyl-5-amino-1-(2,6-dichloro-4-trifluoromethylphenyl)4-ethylsulfinylpyrazole
4. 3-acetyl-1-(2,6-dichloro-4-trifluoromethylphenyl)-5-ethylamino-4-methylsulfinylpyrazole
5. 3-acetyl-1-(2,6-dichloro-4-trifluoromethylphenyl)-5-methylamino-4-methylsulfinylpyrazole
6. 3-acetyl-5-(carbamoylmethylamino)-11-(2,6-dichloro-4-trifluoromethylphenyl)-4-methylsulfinylpyrazole
7. 3-acetyl-1-(2,6-dichloro-4-trifluoromethylphenyl)-5-(2-ethylsulfonylethylamino)-4-methylsulfinylpyrazole
8. 3-acetyl-1-(2,6-dichloro-4-trifluoromethylphenyl)-5-(2-carbamoylmethylamino)-4-methylsulfinylpyrazole
9. 3-acetyl-5-amino-1-(2-bromo-6-chloro-4-trifluoromethylphenyl)-4-methylsulfinylpyrazole
10. 3-acetyl-1-(2,6-dichloro-4-trifluoromethylphenyl)-4-methylsulfinyl-5-trifluoromethylsulfenylaminopyrazole 11. 3-acetyl-5-amino-1-(2,6-dichloro-4-pentafluorothiophenyl)-4-methylsulfinylpyrazole 12. 3-acetyl-5-amino-1-(2,6-dichloro-4-pentafluorothiophenyl)-4-methylthiopyrazole Compounds 1 and 2 are preferred.

Among the compounds which can be used in the invention some are new and are a further feature of the instant invention. The following representative compounds of formula (I) also form part of the invention. In the Table below Et represents ethyl, Pr means n-propyl. Where subscripts are not shown they are intended, for example SCFCl2 means $SCFCl_2$.

METHODS AND PROCESSES OF SYNTHESIS

The compounds of formula (I) can be prepared according to the manufacturing processes described in International Patent Publications Nos. WO 94/21606 and WO 93/06089 or International Patent Publication No. WO 87/03781 as well as in European Patent Publication No. 0295117 and Hatton et al U.S. Pat. No. 5,232,940. Those skilled in the art will choose the proper initial reactant in these known methods and adapt these known methods to the said reactant so as to obtain the corresponding desired products. It is understood that in the description of the following processes the sequences for the introduction of the various groups on

| Cmpd No | $R^1$ | $R^2$ | $R^3$ | $R^4$ | X | m.p. ° C. (about) |
|---|---|---|---|---|---|---|
| 13 | SCFCl2 | NH2 | Cl | CF3 | C—Cl | 136 |
| 14 | SO2CF3 | NH2 | Cl | CF3 | C—Cl | 164 |
| 15 | SCF3 | H | Cl | CF3 | C—Cl | |
| 16 | SCF3 | N=CH(OEt) | Cl | CF3 | C—Cl | |
| 17 | SOCF3 | H | Cl | CF3 | C—Cl | 149 |
| 18 | SO2CF3 | H | Cl | CF3 | C—Cl | 119 |
| 19 | SOCH3 | NH2 | Cl | OCF3 | C—Cl | 147 |
| 20 | SOEt | NH2 | Cl | CF3 | N | 69 |
| 21 | SOCH3 | NH(CH2)2CN | Cl | CF3 | C—Cl | |
| 22 | SOCH3 | NH(CH2)2COCH3 | Cl | CF3 | C—Cl | |
| 23 | SOCH3 | NH2 | Cl | CF3 | N | 92 |
| 24 | SO2CH3 | NH2 | Cl | OCF3 | C—Cl | 211 |
| 25 | SCClF2 | NH2 | Cl | CF3 | C—Cl | 124 |
| 26 | SCH3 | NH2 | Br | CF3 | C—Cl | 99 |
| 27 | SO2CH3 | NH2 | Cl | CF3 | N | 165 |
| 28 | SOCH3 | NH2 | Br | CF3 | C—Br | |
| 29 | SOCH3 | NH2 | H | CF3 | C—Br | 162 |
| 30 | SOCH3 | NH2 | H | CF3 | C—Cl | |
| 31 | SCH3 | NH2 | Cl | OCF3 | C—Cl | 151 |
| 32 | SOCH3 | CH3 | Cl | CF3 | C—Cl | 138 |
| 33 | SOCH3 | NHEt | Br | CF3 | C—Cl | 124 |
| 34 | SOCF3 | NH2 | Cl | CF3 | C—Cl | 177 |
| 35 | SOEt | H | Cl | CF3 | C—Cl | 152 |
| 36 | SO(CH2)2F | NH2 | Cl | CF3 | C—Cl | 140 |
| 37 | SO2Et | NHCH2CONH2 | Cl | CF3 | C—Cl | 212 |
| 38 | SOCH3 | NHCH3 | Br | CF3 | C—Cl | 58 |
| 39 | SOEt | NH(CH2)2SO2Et | Cl | CF3 | C—Cl | 106 |
| 40 | SOCHF2 | NH2 | H | CF3 | C—Cl | 140 |
| 41 | SOPr | NH2 | Cl | CF3 | C—Cl | 147 |
| 42 | SO2CH3 | NH(CH2)2OCH3 | Cl | CF3 | C—Cl | 54 |
| 43 | SOCH3 | NHCH2C(CH3)2OH | Cl | CF3 | C—Cl | 50 |
| 44 | SOCH2F | NH2 | Cl | CF3 | C—Cl | |
| 45 | SOEt | NHCH3 | Cl | OCF3 | C—Cl | 138 |
| 46 | SOCH3 | H | Cl | CF3 | C—Cl | 174 |
| 47 | SO2CH3 | NH2 | Br | CF3 | C—Cl | 199 |
| 48 | SOEt | NH2 | Br | CF3 | C—Br | 176 |
| 49 | SOEt | NH2 | Cl | OCF3 | C—Cl | 165 |
| 50 | SEt | N(CH3)Et | Cl | CF3 | C—Cl | 78 |
| 51 | SEt | NHCH3 | Cl | CF3 | C—Cl | |
| 52 | SOEt | NHCH3 | Cl | CF3 | C—Cl | 148 |
| 53 | SCH3 | OEt | Cl | CF3 | C—Cl | |
| 54 | SO2CH3 | SCH3 | Cl | CF3 | C—Cl | 122 |
| 55 | SCH3 | NH2 | Cl | Cl | N | 110 |
| 56 | SO2CH3 | NH2 | Cl | Cl | N | 200 |
| 57 | SO2Et | NH2 | Cl | CF3 | C—Cl | 178 |
| 58 | SCH3 | NH2 | Br | OCF3 | C—Br | 140 |
| 59 | SOCH3 | NH2 | Cl | Cl | N | 160 |
| 60 | SEt | NH2 | Br | OCF3 | C—Br | |
| 61 | SOEt | NH(CH2)2SO2CH3 | Cl | CF3 | C—Cl | 123 |
| 62 | SPr | NH2 | Cl | CF3 | C—Cl | 89 |
| 63 | SCH3 | NH2 | Br | CF3 | C—Br | 110 |
| 64 | SCH3 | NHCOCF3 | Cl | CF3 | C—Cl | 155 |
| 65 | S(CH2)2Cl | NH2 | Cl | CF3 | C—Cl | 99 |
| 66 | SO2CH3 | NH2 | Cl | SF5 | C—Cl | 250 |
| 67 | SOCH3 | N=CH(OCH3) | Cl | CF3 | C—Cl | 114 |
| 68 | SOCH3 | N(CH3)2 | Cl | CF3 | C—Cl | 129 |
| 69 | SOCH3 | CH2CH2Br | Cl | CF3 | C—Cl | |
| 70 | SCF3 | H | Cl | CF3 | C—Cl | 88 | the pyrazole ring may be performed in a different order and that suitable protecting groups may be required as will be apparent to those skilled in the art.

In the following description of processes when symbols appearing in formulae are not specifically defined, it is to be understood that they are "as defined above" in accordance with the first definition of each symbol in the specification.

According to a further feature of the present invention compounds of general formula (I) wherein $R^1$, $R^2$, $R^3$, $R^4$ and X are as defined above may be prepared by reacting compounds of formula (II):

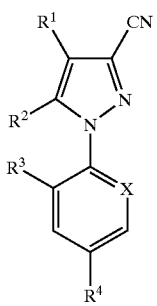

(II)

wherein $R^1$, $R^2$, $R^3$, $R^4$ and X are as defined above with an appropriate reagent CH3M wherein M is an alkali metal such as lithium; or an alkaline earth metal salt such as MgBr, MgCl, MgI in which case the CH3M is a Grignard reagent such as methyl magnesium bromide, methyl magnesium iodide and methyl magnesium chloride. The reaction can be conducted in a variety of solvents for example dichloromethane, dichloromethane, toluene, tetrahydrofuran and chlorobenzene which may be present as a mixture, at a temperature ranging from −70° C. to 120° C., preferably from −20° C. to 50° C. The reaction may be catalyzed by acids including Lewis acid, such as but not limited to $AlCl_3$, $BBr_3$, $TiCl_4$, $BF_3$, $SiCl_4$, $BCl_3$, CuBr.

According to a further feature of the invention compounds of general formula (I) wherein $R^1$, $R^2$, $R^3$, $R^4$ and X are as defined above and m represents 0 or 1 may be prepared directly by reacting the corresponding compounds of formula

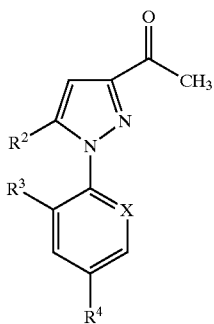

(III)

with an appropriate reagent $R^5S(O)_mY$ wherein m represents 0 or 1 and Y is halogen (preferably chlorine). The transformation of the compounds of formula (III) into compounds of formula(I) can be achieved by the direct sulfenylation or sulfinylation using the appropriate alkylsulfenyl halides or alkylsulfinyl halides, such as methylsulfenyl halide or methylsulfinyl halide. The alkylsulfenyl halides and alkylsulfinyl halides can be prepared in a separate pot or optionally in situ in the medium used for reaction with the compounds of formula (III). Inert solvents are generally used for example methyl t-butyl ether, dichloroethane; toluene and chlorobenzene. The reaction can be conducted in the presence of catalyst which may be basic, for example a metal carbonate, a metal hydride such as a sodium hydride, or a metal hydroxide such as a sodium hydroxide. The reaction can be carried out at a temperature from about −20° C. to about 120° C., preferably at a temperature of from 0° C. to 100° C.

According to a further feature of the invention compounds of general formula (I) wherein $R^1$, $R^3$, $R^4$ and X are as defined above and $R^2$ represents amino may be prepared by the reaction of a compound of formula (IV):

(IV)

with a compound of formula (V):

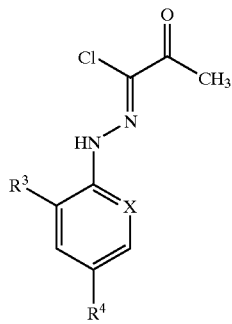

(V)

The reaction is performed in the presence of a base for example a metal alkoxide preferably sodium ethoxide in an inert solvent for example ethanol at a temperature from 0° C. to the reflux temperature.

According to a further feature of the invention compounds of general formula (I) wherein $R^1$, $R^2$, $R^3$, $R^4$ and X are as defined above and wherein m represents 1 or 2 may be prepared by the oxidation of the corresponding compounds of formula (I) in which m represents 0 or 1. The reaction is preferably performed with a peracid such as 3. -chloroperbenzoic acid in an inert solvent for example methylene chloride at a temperature from 0° C. to the reflux temperature of the solvent.

According to a further feature of the present invention compounds of general formula (I) wherein $R^2$ represents $NR^6R^7$, $—S(O)_nR^8$, $C(O)OH$, alkyl, haloalkyl, or
—N=$C(R^{10})(R^{11})$ wherein $R^6$ and/or $R^7$ represent alkyl, haloalkyl, —$C(O) R^8$, $C(O)OR^8$, and —$S(O)_qCF_3$; the alkyl portions of which are optionally substituted by one or more $R^{12}$; or $R^6$ and $R^7$ are joined so as together form a divalent radical having 4 to 6 atoms in the chain, may be prepared from the corresponding compounds in which $R^2$ is amino by methods described in one or more of International Publications No. WO 94/21606, WO 93/06089 and WO 87/03781, European Patent Publication No. 0295117 and EP 511845, Hatton et al U.S. Pat. No. 5,232,940, German Patent Publication No. DE 19511269, and EP 780378.

According to a further feature of the invention compounds of general formula (I) wherein $R^1$, $R^3$, $R^4$ and X are as defined above and $R^2$ represents $NR^6R^7$ wherein $R^6$ represents hydrogen and $R^7$ represents ethyl substituted at the 2-position by $R^{12}$ wherein $R^{12}$ represents cyano, nitro, $-S(O)_sR^8$, $C(O)R^8$, $C(O)OR^9$, aminocarbonyl, alkylaminocarbonyl, dialkylaminocarbonyl, aminosulfonyl, alkylaminosulfonyl or dialkylaminosulfonyl, may be prepared by the reaction of the corresponding compound of formula (I) wherein $R^2$ is amino with a compound of formula (VI):

(VI)

wherein $R^{12}$ is defined above. The reaction may be performed optionally in the presence of a base such as sodium hydride, an alkali metal hydroxide for example potassium hydroxide, or a tetraalkylammonium hydroxide for example N-benzyltrimethylammonium hydroxide in a solvent such as toluene, ethanol or water, and at a temperature from $-20°$ C. to the reflux temperature.

According to a further feature of the invention compounds of general formula (I) wherein $R^1$, $R^3$, $R^4$ and X are as defined above and $R^2$ represents $NR^6R^7$ wherein $R^6$ and/or $R^7$ represent alkyl or haloalkyl optionally substituted by one or more $R^{12}$, may be prepared by the reaction of the corresponding compound of formula (I) wherein $R^2$ is amino with a compound of formula (VII):

(VII)

wherein $R^{14}$ is alkyl or haloalkyl optionally substituted by one or more $R^{12}$ and Y represents a leaving group preferably halogen for example chlorine. The reaction is performed in the presence of a base such as potassium hydroxide, potassium methoxide, sodium hydride or triethylamine in an inert solvent such as methyl t-butyl ether or toluene, and at a temperature from $-20°$ C. to the reflux temperature.

According to a further feature of the present invention compounds of general formula (I) wherein $R^2$ represents $C(O)OR^8$ may be prepared by the reaction of the corresponding compound of formula (I) in which $R^2$ is carboxy with an alcohol of formula (VIII):

$R^8OH$ (VIII)

The above reaction is generally performed in the presence of an acid catalyst such as sulphuric acid generally in the presence of excess of the alcohol or optionally in a co-solvent at a temperature from $0°$ C. to the reflux temperature. Alternatively the reaction may be performed using a coupling reagent such as dicyclohexylcarbodiimide (DCC) in an inert solvent.

According to a further feature of the present invention compounds of general formula (I) wherein $R^2$ represents carboxy may be prepared by the oxidation of the corresponding compound of formula (I) in which $R^2$ is replaced by formyl. The reaction is generally carried out using potassium permanganate or chromic acid in a solvent such as water at $0°$ C. to the reflux temperature.

According to a further feature of the present invention compounds of general formula (I) wherein $R^2$ represents $R^aCH(Cl)CH_2-$ wherein $R^a$ represents alkyl may be prepared by the diazotisation of the corresponding compound of formula (I) in which $R^2$ represents amino and reaction with a compound of formula (IX):

(IX)

The reaction is generally carried out using an alkyl nitrite such as tert-butyl nitrite in the presence of a copper salt such as copper (II) chloride in a solvent such as acetonitrile at a temperature from $-10°$ C. to $50°$ C.

According to a further feature of the present invention compounds of general formula (I) wherein $R^2$ represents $C(O)R^8$ may be prepared by the oxidation of the corresponding compound of formula (X):

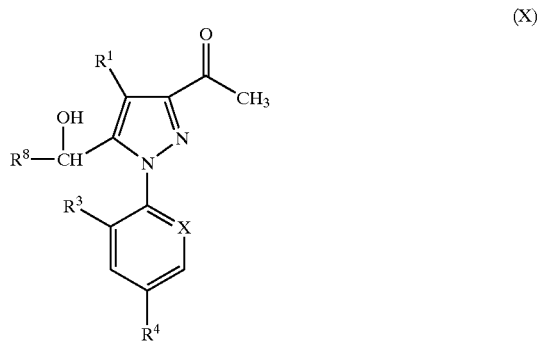
(X)

wherein $R^1$, $R^3$, $R^4$, $R^8$ and X are as defined above. The reaction may be performed using for example a mixture of chromic acid and sulphuric acid in a solvent such as water and acetone at a temperature from $0°$ C. to $60°$ C.

According to a further feature of the present invention compounds of general formula (I) wherein $R^2$ represents $OR^9$ may be prepared by methods described in U.S. Pat. Nos. 5,047,550 and 4,918,085.

Intermediates of formula (II) wherein $R^1$ represents $S(O)_mR^5$ and wherein m represents 1 or 2 may be prepared by the reaction of a compound of formula (XI):

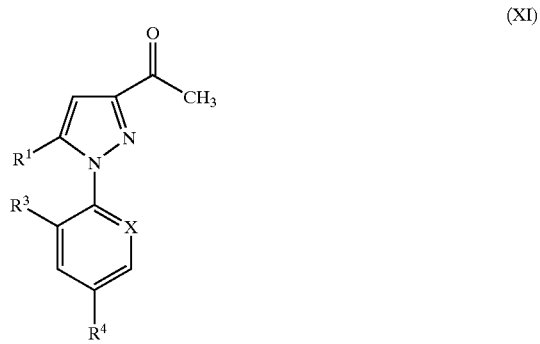
(XI)

with a reagent of formula $R^5S(O)_mY$ wherein Y represents halogen preferably chlorine using the above described method for the preparation of compounds of formula (I) from compounds of formula III).

Intermediates of formula (III) wherein $R^2$ is amino can be prepared by diazotisation of a compound of formula (XII):

(XII)

and reaction of the resultant diazonium salt of formula with a reagent of formula (XIII):

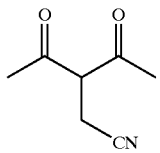

(XIII)

The diazotisation of compounds of formula (II) may be performed by well documented procedures. The reaction of the diazonium salts with compounds of formula (XIII) to give compounds of formula (III) wherein $R^2$ is amino can be achieved via a two step process involving coupling and subsequent ring closure which may be performed in the same vessel. The condensation can be achieved in the presence of appropriate acids such as acetic acid or hydrochloric acid or in the presence of a basic catalyst such as sodium acetate. The reaction can be carried out in a variety of solvents including alcohols such as ethanol or ethers such as methyl t-butyl ether, optionally in admixture with water, generally at a temperature from about −30° C. to 100° C. preferably from 0° C. to 50° C. The ring closure step is preferably carried out in the presence of base catalyst in appropriate solvents including but not limited to those employed in the first (coupling) stage of the reaction. The base catalyst used can be an organic base for example triethylamine or pyridine; amidines such as 1,8-diazabicyclo (5.4.0)undec-7-ene (DBU) or an inorganic base such as ammonia, sodium bicarbonate or sodium hydroxide. The reaction can be conducted from about −30° C. to about 120° C., preferably from 0° C. to 100° C.

Intermediates of formula (X) can be prepared by reaction of the corresponding compounds of formula (I) in which $R^2$ is replaced by a formyl group with an organometallic reagent of formula $R^8 Q$ wherein Q is preferably an alkali or alkaline earth metal for example a magnesium halide (Grignard) reagent. The reaction may be performed in an inert solvent such as methyl t-butyl ether at a temperature from −78° C. to the reflux temperature of the solvent.

Intermediates of formula (I) in which $R^2$ is replaced by a formyl group may be prepared by the oxidation of the corresponding compound of formula (I) in which $R^2$ represents $R^a CH=CH-$. The reaction is generally performed using a reagent such as ozone or sodium metaperiodite in an inert solvent for example dichloroethane at a temperature from −100° C. to 100° C.

Intermediates of formula (I) in which $R^2$ is replaced by $R^a CH=CH-$ may be prepared by the dehydrochlorination of the corresponding compound of formula (I) in which $R^2$ represents $R^a CH(Cl)CH_2-$. The reaction is generally performed using a base such as sodium hydroxide or triethylamine in an inert solvent for example dichloroethane at a temperature from −70° C. to the reflux temperature.

Synthesis of intermediate compounds of general formula (XII) can be achieved according to variations of known methods, for example, those described in WO 93/06089, as well as in Hatton et al U.S. Pat. No. 5,232,940.

Certain compounds of formula (II) are novel and as such form a further feature of the present invention.

Intermediates of formula (IV) and (V) are known or may be prepared by known methods.

The invention is illustrated by the following examples which are not considered as limiting the invention but are given to better enable use of it.

EXAMPLE 1

To a suspension of 1-(2,6-dichloro-4-trifluoromethylphenyl)-5-amino-3-cyano-4-methylsulfinylpyrazole (2 g) in toluene was added methyl magnesium bromide (7 ml of a 1.4M solution in toluene/THF). The mixture was stirred at 20° C. (1 hr.) and neutralized with saturated ammonium chloride solution. The organic layer was dried (sodium sulfate), evaporated and the residue purified by chromatography using 40% ethyl acetate in hexane to give 3-acetyl-5-amino-1-(2,6-dichloro-4-trifluoromethylphenyl)-4-methylsulfinylpyrazole (Compound 1, 0.68 g), m.p. 166° C.

By proceeding in a similar manner the compounds of formula (I) shown in the following Table were also obtained. In the Table Et means ethyl.

| Cmpd No. | $R^1$ | $R^2$ | $R^3$ | $R^4$ | X | m.p. ° C. |
|---|---|---|---|---|---|---|
| 2 | $SCH_3$ | $NH_2$ | Cl | $CF_3$ | C—Cl | 113 |
| 3 | SOEt | $NH_2$ | Cl | $CF_3$ | C—Cl | 189 |
| 4 | $SOCH_3$ | NHEt | Cl | $CF_3$ | C—Cl | 123 |
| 5 | $SOCH_3$ | $NHCH_3$ | Cl | $CF_3$ | C—Cl | 126 |
| 6 | $SOCH_3$ | $NHCH_2CONH_2$ | Cl | $CF_3$ | C—Cl | 165 |
| 7 | $SOCH_3$ | $NH(CH_2)_2SO_2Et$ | Cl | $CF_3$ | C—Cl | 102 |
| 8 | $SOCH_3$ | $NH(CH_2)_2CONH_2$ | Cl | $CF_3$ | C—Cl | 132 |
| 9 | $SOCH_3$ | $NH_2$ | Br | $CF_3$ | C—Cl | 153 |
| 11 | $SOCH_3$ | $NH_2$ | Cl | $SF_5$ | C—Cl | 166 |
| 12 | $SCH_3$ | $NH_2$ | Cl | $SF_5$ | C—Cl | 150 |

EXAMPLE 2

To a solution of 3-acetyl-5-amino-1-(2,6-dichloro-4-trifluoromethylphenyl)-4-methylsulfinylpyrazole (3 g) in dichloromethane containing diisopropylethylamine (1.44 ml) was added trifluoromethylsulfenyl chloride (0.97 ml) at −30° C. The mixture was stirred (2 hours) and when at 20° C. purged with nitrogen. Water was added and the organic phase dried (sodium sulfate) and evaporated. The residue was purified by silica gel chromatography eluting with 25% ethyl acetate in hexane to give 3-acetyl-1-(2,6-dichloro-4-trifluoromethylphenyl)-4-methylsulfinyl-5-trifluoromethylsulfenylaminopyrazole (Compound 10, 0.5 g), m.p. 67–102° C., mass spectral analysis $M^+/e=499$.

REFERENCE EXAMPLE 1

To a solution of 5-amino-3-cyano-1-(2,6-dichloro-4-trifluoromethylphenyl)-4-ethylthiopyrazole (22.25 g) in methanol was added a solution of sulfuric acid (1.5 g) in isopropanol. Hydrogen peroxide (6.95 g of 30% aqueous solution) was added and the temperature raised to 60° C. After two hours, the reaction was filtered and the solid washed with methanol. The filtrate was washed (water), dried and recrystallized (methanol) to give 5-amino-3-cyano-1-(2,6-dichloro-4-trifluoromethylphenyl)-4-ethylsulfinylpyrazole (18.4 g), m.p. 173–174° C.

REFERENCE EXAMPLE 2

To a suspension of 1-(2,6-dichloro-4-trifluoromethylphenyl)-3-cyano-4-methylsulfinyl-5-[1-methoxy(ethylene-imino]pyrazole (6 g) in methanol was added sodium borohydride (0.79 g) in three portions over 15 min. at 20° C. and stirred under a nitrogen atmosphere for 45 min. The mixture was evaporated and the residue purified by flash column chromatography on silica gel using 15% ethyl acetate in methylene chloride to give 1-(2,6-dichloro-4-trifluoromethylphenyl)-3-cyano-5-ethylamino-4-methylsulfinylpyrazole (1.1 g) m.p. 130–131° C.(decomposition).

REFERENCE EXAMPLE 3

To a solution of 5-amino-1-(2,6-dichloro-4-pentafluorothiophenyl)-3-cyano-4-methylthiopyrazole (20 mg) in methanol was added sulfuric acid/isopropanol catalyst solution (0.02 ml), followed by 30% hydrogen peroxide (0.02 ml) at 4° C. The mixture was stirred for 2 days at 20° C. Further $H_2SO_4$/isopropanol solution and hydrogen peroxide were added, the mixture stirred overnight and partitioned between methylene chloride and water. The organic layer was washed with sodium bisulfite solution, sodium bicarbonate solution and water. The organic layer was dried (sodium sulfate), evaporated and the residue purified by preparative TLC using 70% ethyl acetate in hexane to give the 5-amino-1-(2,6-dichloro-4-pentafluorothiophenyl)-3-cyano-4-methylsulfinylpyrazole. H-1 NMR(CDCl$_3$): 7.8 ppm (2H, d), 3.0.ppm (3H, s).

REFERENCE EXAMPLE 4

I) Preparation of methylsulfenyl chloride:

Sulfuryl chloride (1.48 g) was added to a solution of dimethyldisulfide (3.16 g) in methyl t-butyl ether. The mixture was stirred at 20° C. for 5 hours. A 0.6 ml portion of the resultant solution was used in the following reaction.

II) Methylsulfenylation:

5-Amino-1-(2,6-dichloro-4-pentafluorothiophenyl)-3-cyanopyrazole (40 mg) was heated to reflux under an inert atmosphere in methyl t-butyl ether. Methylsulfenyl chloride (0.6 ml solution in methyl-t-butyl ether) was added and the mixture was heated at reflux (4 hours). The cooled mixture was partitioned between saturated sodium bicarbonate solution and methylene chloride. The organic layer was washed (water), dried (sodium sulfate), evaporated and the residue purified by preparative TLC using 40% ethyl acetate in hexane to give 5-amino-1-(2,6-dichloro-4-pentafluorothiophenyl)-3-cyano-4-methylthiopyrazole. H-1 NMR(CDCl$_3$): 7.8 ppm (2H, s), 2.3 ppm (3H, s).

REFERENCE EXAMPLE 5

A solution of 5-amino-1-(2,6-dichloro-4-trifluoromethylphenyl)-3-cyano-4-methylsulfinylpyrazole (10 g) in dry DMF was added during 10 minutes to potassium hydride (0.7 g of a 35% suspension in oil) in dry DMF at 4° C. and stirred for 20 min. Vinyl ethyl sulfone (3.13 g) in dry DMF was added. over 5 hr at 4° C. and the mixture stirred overnight whilst warming to 20° C. under a nitrogen atmosphere. The mixture was recooled, ammonium chloride solution added and the organic layer washed (water), dried (sodium sulfate) and evaporated. The residue was crystallized (ethyl acetate/hexane) to give 1-(2,6-dichloro-4-trifluoromethylphenyl)-3-cyano-5-(2-ethylsulfonylethylamino)-4-methylsulfinylpyrazole (4.08 g), m.p. 131–132° C.

Further intermediate 3-cyanopyrazole derivatives of general formula (II) used in Example 1 are known or were prepared by choosing the proper reactant with the proper formula, for example as described in EP 0295117 and U.S. Pat. No. 5,232,940 and are shown in the Table below in which Et represents ethyl.

| $R^1$ | $R^2$ | $R^3$ | $R^4$ | X | m.p ° C. |
|---|---|---|---|---|---|
| SOCH$_3$ | NHCH$_3$ | Cl | CF$_3$ | C—Cl | 147–150 |
| SOCH$_3$ | NHCH$_2$CONH$_2$ | Cl | CF$_3$ | C—Cl | 155–157 |

-continued

| $R^1$ | $R^2$ | $R^3$ | $R^4$ | X | m.p ° C. |
|---|---|---|---|---|---|
| SOCH$_3$ | NH(CH$_2$)$_2$CONH$_2$ | Cl | CF$_3$ | C—Cl | 159–160 |
| SOCH$_3$ | NH$_2$ | Br | CF$_3$ | C—Cl | 150–151 |

The following test method is representative of the mammalian toxicity. A similar test conducted with housefly heads instead of rat brain is representative of the toxicity in insects.

GABA Receptor Test

Rat brains were homogenized with physiological saline (same pH as in rat plasma). 0.1 ml of such a suspension was mixed with a radioligand [4'-ethynyl-4-n-propyl bicycloorthobenzoate (EBOB)]. Tubes containing this mixture and a test compound were compared with a reference (tubes with this mixture but without test compound).

All tubes were incubated (90 min; 20° C.). The content was filtered and the radioactivity remaining on the filter was determined. The concentration of test compound which inhibited 50% of the controlled binding was the IC-50 of the compound.

The radioligand binds to a site within the known GABA receptor channel. If there is no test compound, the radioligand does bind; if there is a toxic compound effective upon the same site, the amount of radioligand is reduced because the radioligand is replaced by the tested toxic compound.

In the above in vivo test on the GABA receptor channel, compounds of the invention were active at a very high concentration (high IC 50) which is deemed to show that the compounds are still safe for mammals even when toxic to insects. The following test methods were used applying representative compounds of the invention hereinabove prepared. The following species were used:

| GENUS, SPECIES | COMMON NAME | ABBREVIATION |
|---|---|---|
| Aphis gossypii | cotton leaf aphid | APHIGO |
| Schizaphis graminum | greenbug | TOXOGR |
| Musca domestica | housefly | MUSCDO |
| Meloidogyne incognita | southern root-knot nematode | MELGIN |

The Soil Drench Method

Cotton and sorghum plants were established in pots. One day prior to treatment, each pot was infested with about 25 aphids of a mixed population. Cotton plants were infested with cotton leaf aphid and sorghum plants were infested with greenbug. Test compound was applied to the soil surface as solutions that delivered the equivalent of 20, 5 and 1.25 ppm soil concentration by weight. Aphid counts were obtained at 5 DAT (days after treatment). The number of aphids on the treated plants was compared to the number of those on the untreated control plants.

Compound numbers 1–12 gave effective control of Aphis gossypii at a dose of 2.5 ppm or less. Compound numbers 1–7 and 9–12 gave effective control of Schizaphis graminum at a dose of 2.5 ppm or less.

Nematode Soil Drench Method

Soil is treated with the test compound to obtain a soil concentration of 10.0 ppm. Juveniles collected and separated from infected tomato roots are introduced to the treated soil. The treated and nematode-infested soil are either planted with tomato seedlings or cotton seeds (both susceptible to nematode attack). After the appropriate interval for plant growth and root-knot formation, the plants are removed from the soil and the roots examined for root-knot formation. Untreated, uninoculated plants has roots free of knots as do plants where the test compounds elicit high activity.

The Housefly Bait/Contact Test

About 25 four to six day old adult houseflies were anesthetized and placed in a cage with a sugar water bait solution containing the test compound. The compound concentration in the bait solution was 100 ppm. After 24 hours, flies which showed no movement on stimulation were considered dead.

A 100% mortality was obtained with representative compounds of the invention.

The present invention provides a method for the systemic control of arthropods at a locus, especially some insects or mites which feed on the above ground portions of plants. Control of such foliar pests may be provided by direct foliar application or by application by for example soil spray or granule application to the plant roots or plant seeds with subsequent systemic translocation to the above ground portions of the plants. Such systemic activity includes the control of insects which reside not only at the point of application but at a remote part of the plant for example by translocation from one side of a leaf to the other or from a treated leaf to an untreated leaf. Examples of the classes of insect pests which may be systemically controlled by the compounds. of the invention include the Homoptera order (piercing-sucking), Hemiptera order (piercing-sucking), and Thysanoptera order. The invention is especially appropriate for aphids and thrips.

As is evident from the foregoing pesticidal uses, the present invention provides pesticidally active compounds and methods of use of said compounds for the control of a number of pest species which includes: arthropods, especially insects or mites; plant nematodes; or helminth or protozoan pests. The compounds of formula (I) or pesticidally acceptable salts thereof thus are advantageously employed in practical uses, for example, in agricultural or horticultural crops, forestry, veterinary medicine or livestock husbandry, or in public health. From this point forward, whenever the term "compounds of formula (I)" is used this term embraces compounds of formula (I) and their pesticidally acceptable salts. The term "compound of formula (I)" embraces a compound of formula (I) and a pesticidally acceptable salt thereof.

The present invention therefore provides a method of control of pests at a locus which comprises the treatment of the locus (e.g., by application or administration) with an effective amount of a compound of formula (I) or a pesticidally acceptable salt thereof, wherein the substituent groups are as hereinbefore defined. The locus includes, for example, the pest itself or the place (plant, animal, field, structure, premises, forest, orchard, waterway, soil, plant or animal product, or the like) where the pest resides or feeds.

The compounds of this invention may in addition be used to control soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

Compounds of the invention may be used in the following applications and on the following pests including arthropods, especially insects or mites, nematodes, or helminth or protozoan pests:

In the protection of stored products, for example cereals, including grain or flour, groundnuts, animal feedstuffs, timber or household goods, e.g. carpets and textiles, compounds of the invention are useful against attack by arthropods, more especially beetles, including weevils, moths or mites, for example Enhestia spp. (flour moths), Anthrenus spp. (carpet beetles), Tribolium spp. (flour beetles), Sitophilus spp. (grain weevils) or Acarus spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, Reticuliternes spp., Heterotermes spp., Coptotermes spp. In agriculture against adults, larvae and eggs of Lepidoptera (butterflies and moths), e.g. Heliothis spp. such as *Heliothis virescens* (tobacco budworm), *Heliothis armigera* and *Heliothis zea*. Against adults and larvae of Coleoptera (beetles) e.g. Anthonomus spp. e.g. *grandis* (cotton boll weevil), *Leptinotarsa decemlineata* (Colorado potato beetle), Diabrotica spp. (corn rootworms). Against Heteroptera (Hemiptera and Homoptera) e.g. Psylla spp., Bemisia spp., Trialeurodes spp., Aphis spp., Myzus spp., *Megoura viciae*, Phylloxera spp., Nenhotettix spp. (rice leaf hoppers), Nilaparvata spp.

Against Diptera e.g. Musca spp. Against Thysanoptera such as *Thrips tabaci*. Against Orthoptera such as Locusta and Schistocerca spp., (locusts and crickets) e.g. Gryllus spp., and Acheta spp. for example, Blatta orientalis, *Periplaneta americanas Blatella germanica Locusta migratoria migratorioides*, and *Schistocerca gregaria*. Against Collembola e.g. Periplaneta spp. and Blattela spp. (roaches). Against Isoptera e.g. Coptotermes spp. (termites).

Against arthropods of agricultural significance such as Acari (mites) e.g. Tetranychus spp., and Panonychus spp.

Against nematodes which attack plants or trees of importance to agriculture, forestry or horticulture either directly or by spreading bacterial, viral, mycoplasma or fungal diseases of the plants. For example root-knot nematodes such as Meloidomne spp. (e.g. *M. incognita*).

In the field of veterinary medicine or livestock husbandry or in the maintenance of public health against arthropods, helminths or protozoa which are parasitic internally or externally upon vertebrates, particularly warm-blooded vertebrates, for example domestic animals, e.g. cattle, sheep, goats, equines, swine, poultry, dogs or cats, for example Acarina, including ticks (e.g. Ixodes spp., Boophilus spp. e.g. *Boophilus microplus*, Rhipiceghalus spp. e.g. *Rhipiceohalus appendiculatus* Omithodorus spp. (e.g. *Ornithodorus moubata*) and mites (e.g. Damalinia spp.); Diptera (e.g. Aedes spp., Anonheles spp., Musca spp., Hypoderma spp.); Hemiptera.; Dictyoptera (e.g. Periplaneta spp., Blatella spp.); Hymenoptera; for example against infections of the gastro-intestinal tract caused by parasitic nematode worms, for example members of the family Trichostrongylidae; in the control and treatment of protozoal diseases caused by, for example, Eimeria spp. e.g. *Trypanosoms cruzi*, Leishaminia spp., Plasmodium spp., Babesis spp., Trichomonadidae spp., Toxoplasma spp. and Theileria spp.

In practical use for the control of arthropods, especially insects or mites, or nematode pests of plants, a method, for example, comprises applying to the plants or to the medium in which they grow an effective amount of a compound of the invention. For such a method, the active compound is generally applied to the locus in which the arthropod or nematode infestation is to be controlled at an effective rate in the range of about 5 g to about 1 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. More preferably an effective rate range of the active compound is from about 50 g/ha to about 400 g/ha.

When a pest is soil-borne, the active compound generally in a formulated composition, is distributed evenly over the area to be treated (ie, for example broadcast or band treatment) in any convenient manner and is applied at rates from about 5 to about 1 kg ai/ha, preferably from about 50 to about 250 g ai/ha. When applied as a root dip to seedlings or drip irrigation to plants the liquid solution or suspension contains from about 0.075 to about 1000 mg ai/l, preferably from about 25 to about 200 mg ai/l. Application may be made, if desired, to the field or crop-growing area generally or in close proximity to the seed or plant to be protected from attack. The active component can be washed into the soil by spraying with water over the area. or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting.

The compounds of the invention and methods of control of pests therewith are of particular value in the protection of field, forage, plantation, glasshouse, orchard or vineyard crops, of ornamentals, or of plantation or forest trees, for example: cereals (such as wheat or rice), cotton, vegetables (such as peppers), field crops (such as sugar beets, soybeans or oil seed rape), grassland or forage crops (such as maize or sorghum), orchards or groves (such as of stone or pit fruit or citrus), ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compounds of the invention and methods of use thereof are of particular value in the control of arthropods, helminths or protozoa which are injurious to, or spread or act as vectors of diseases domestic animals, for example those hereinbefore mentioned, and more especially in the control of ticks, mites, lice, fleas, midges, or biting, nuisance or myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

Furthermore, compounds of the invention may be useful for coccidiosis, a disease caused by infections from protozoan parasites of the genus Eimeria. It is an important potential cause of economic loss in domestic animals and birds, particularly those raised or kept under intensive conditions. For example, cattle, sheep, pigs or rabbits may be affected, but the disease is especially important in poultry, particularly in chickens. Administration of a small amount of a compound of the invention, preferably by a combination with feed is effective in preventing or greatly reducing the incidence of coccidiosis. The compounds are effective against both the cecal form and the intestinal forms. Furthermore, the compounds of the invention may also exert an inhibiting effect on oocytes by greatly reducing the number and sporulation of those produced. The poultry disease is generally spread by the birds picking up the infectious organism in droppings in or on contaminated litter, ground, food, or drinking water. The disease is manifested by hemorrhage, accumulation of blood in the ceca, passage of blood to the droppings, weakness and digestive disturbances. The disease often terminates in the death of the animal, but the fowl which survive severe infections have had their market value subtantially reduced as a result of the infection.

The compositions hereinafter described for application to growing crops or crop growing loci or as a seed dressing may, in general, alternatively be employed for topical application to animals or in the protection of stored products, household goods, property or areas of the general environment. Suitable means of applying the compounds of the invention include:

to growing crops as foliar sprays, dusts, granules, fogs or foams or also as suspensions of finely divided or encapsulated compositions as soil or root treatments by liquid drenches, dusts, granules, smokes or foams; to seeds of crops via application as seed dressings by liquid slurries or dusts;

to animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;

to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water;

to domestic animals in feed to control fly larvae feeding in their feces;

In practice, the compounds of the invention most frequently form parts of compositions. These compositions can be employed to control: arthropods, especially insects or mites; nematodes; or helminth or protozoan pests. The compositions may be of any type known in the art suitable for application to the desired pest in any premises or indoor or outdoor area or by internal or external administration to vertebrates. These compositions contain at least one compound of formula (I) or a pesticidally acceptable salt thereof, such as described earlier, as the active ingredient in combination or association with one or more other compatible components which are for example, solid or liquid carriers or diluents, adjuvants, surface-active-agents, or the like appropriate for the intended use and which are agronomically or medicinally acceptable. These compositions, which may be prepared by any manner known in the art, likewise form a part of this invention.

These compositions may also contain other kinds of ingredients such as protective colloids, adhesives, thickeners, thixotropic agents, penetrating agents, spray oils (especially for acaridical use), stabilizers, preservative agents (especially mold preservatives), sequestering agents, or the like, as well as other known active ingredients with pesticidal properties (particularly insecticidal, miticidal, nematicidal, or fungicidal) or with properties regulating the growth of plants. More generally, the compounds employed in the invention may be combined with all the solid or liquid additives corresponding to the usual techniques of formulation.

Compositions, suitable for applications-in agriculture, horticulture, or the like include formulations suitable for use as, for example, sprays, dusts, granules, fogs, foams, emulsions, or the like.

The effective use doses of the compounds employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminum or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; Water soluble polymers, resins, waxes; or solid fertilizers. Such solid compositions may, if desired, contain one or more compatible wetting, dispersing, emulsifying or coloring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar-solvents such as dimethylformamide, dimethyl sulphoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain other additives such as adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs;. or trace nutrients such as salts of iron, manganese, boron, copper, cobalt, molybdenum or zinc.

Compositions containing compounds of formula (I), or pesticidally acceptable salts thereof, which may be applied to control arthropod,. plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate, e.g. benomyl and iprodione), bactericides, arthropod or vertebrate attractants or repellents or pheromones, deodorants, flavoring agents, dyes, or auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with the compositions of the present invention are: acephate, chlorpyrifos, demeton-S-methyl, disulfoton, ethoprofos, fenitrothion, fenamiphos, fonofos, isazophos, isofenphos, malathion, monocrotophos, parathion, phorate, phosalone, pirimlphos-methyl, terbufos, triazophos, cyfluthrin, cypermethrin, deltamethrin, fenpropathrin, fenvalerate, permethrin, tefluthrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorvos, diaveridine or dimetriadazole.

For their agricultural application, the compounds of the formula (I), or pesticidally acceptable salts thereof, are therefore generally in the form of compositions, which are in various solid or liquid forms.

Solid forms of compositions which can be used are dusting powders (with a content of the compound of formula (I), or a pesticidally acceptable salt thereof, ranging up to 80%), wettable powders or granules (including water dispersible granules), particularly those obtained by extrusion, compacting, impregnation of a granular carrier, or granulation starting from a powder (the content of the compound of formula (I), or a pesticidally acceptable salt thereof, in these wettable powders or granules being between about 0.5 and about 80%). Solid homogenous or heterogenous compositions containing one or more compounds of formula (I), or pesticidally acceptable salts thereof, for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The compounds or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble Some organic solids or inorganic salts may be dissolved in the carrier to help prevent-settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod, plant nematode, helminth or protozoan pests usually contain from about 0.00001% to about 95%, more particularly from about 0.0005% to about 50% by weight of one or more compounds of formula (I), or pesticidally acceptable salts thereof, or of total active ingredients (that is to say the compound of formula (I), or a pesticidally acceptable salt thereof, together with: other substances toxic to arthropods or plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more compounds of formula (I) or pesticidally acceptable salts thereof. For administration to animals orally or parenterally, including percutaneously solid or liquid compositions, these normally contain from about 0.1% to about 90% by weight of one or more compounds of formula (I) or pesticidally acceptable salts thereof. Medicated feedstuffs normally contain from about 0.001% to about 3% by weight of one or more compounds of formula (I) or pesticidally acceptable salts thereof. Concentrates or supplements for mixing with feedstuffs normally contain from about 5% to about 90%, preferably from about 5% to about 50%, by weight of one or more compounds of formula (I) or pesticidally acceptable salts thereof. Mineral salt licks normally contain from about 0.1% to about 10% by weight of one or more compounds of formula (I) or pesticidally acceptable salts thereof.

Dusts or liquid compositions for application to livestock, goods, premises or outdoor areas may contain from about 0.0001% to about 15%, more especially from about 0.005% to about 2.0%, by weight, of one or more compounds of formula (I) or pesticidally acceptable salts thereof. Suitable concentrations in treated waters are between about 0.0001 ppm and about 20 ppm, more particularly about 0.001 ppm to about 5.0 ppm. of one or more compounds of formula (I), or pesticidally acceptable salts thereof, and may be used therapeutically in fish farming with appropriate exposure times. Edible baits may contain from about 0.01% to about 5%, preferably from about 0.01% to about 1.0%, by weight, of one or more compounds of formula (I) or pesticidally acceptable salts thereof.

When administered to vertebrates parenterally, orally or by percutaneous or other means, the dosage of compounds of formula (I), or pesticidally acceptable salts thereof, will depend upon the species, age, or health of the vertebrate and upon the nature and degree of its actual or potential infestation by arthropod, helminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 2A–2M illustrate compositions for use against arthropods, especially mites or insects, plant nematodes, or helminth or protozoan pests which comprise; as-active ingredient, compounds of formula (I), or pesticidally acceptable salts thereof, such as those described in preparative examples. The compositions described in EXAMPLES 2A–2M can each be diluted to give a sprayable compositon at concentrations suitable for use in the field. Generic chemical descriptions of the ingredients (for which all of the following percentages are in weight percent), used in the composition EXAMPLES 2A–2M exemplified below, are as follows:

| Trade Name | Chemical Description |
| --- | --- |
| Ethylan BCP | Nonylphenol ethylene oxide condensate |
| Soprophor BSU | Tristyrylphenol ethylene oxide condensate |

| Trade Name | Chemical Description |
| --- | --- |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan No2 | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

EXAMPLE 2A

A water soluble concentrate is prepared with the composition as follows:

| | |
| --- | --- |
| Active ingredient | 7% |
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

EXAMPLE 2B

An emulsifiable concentrate (EC) is prepared with the composition as follows:

| | |
| --- | --- |
| Active ingredient | 25% (max) |
| Soprophor BSU | 10% |
| Arylan CA | 5% |
| N-methylpyrrolidone | 50% |
| Solvesso 150 | 10% |

The first three components are dissolved in N-methylpyrrolidone and to this is then added the Solvesso 150 to give the final volume.

EXAMPLE 2C

A wettable powder (WP) is prepared with the composition as follows:

| | |
| --- | --- |
| Active ingredient | 40% |
| Arylan S | 2% |
| Darvan No2 | 5% |
| Celite PF | 53% |

The ingredients are mixed and ground in a hammer-mill to a powder with a particle size of less than 50 microns.

EXAMPLE 2D

An aqueous-flowable formulation is prepared with the composition as follows:

| | |
|---|---|
| Active ingredient | 40.00% |
| Ethylan BCP | 1.00% |
| Sopropon T360. | 0.20% |
| Ethylene glycol | 5.00% |
| Rhodigel 230. | 0.15% |
| Water | 53.65% |

The ingredients are intimately mixed and are ground in a bead mill until a mean particle size of less than 3 microns is obtained.

EXAMPLE 2E

An emulsifiable suspension concentrate is prepared with the composition as follows:

| | |
|---|---|
| Active ingredient | 30.0% |
| Ethylan BCP | 10.0% |
| Bentone 38 | 0.5% |
| Solvesso 150 | 59.5% |

The ingredients are intimately mixed and ground in a beadmill until a mean particle size of less than 3 microns is obtained.

EXAMPLE 2F

A water dispersible granule is prepared with the composition as follows:

| | |
|---|---|
| Active ingredient | 30% |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

EXAMPLE 2G

A dusting powder is prepared with the composition as follows:

| | |
|---|---|
| Active ingredient | 1 to 10% |
| Talc powder—superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

EXAMPLE 2H

An edible bait is prepared with the composition as follows:

| | |
|---|---|
| Active ingredient | 0.1 to 1.0% |
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

EXAMPLE 2I

A solution formulation is prepared with a composition as follows:

| | |
|---|---|
| Active ingredient | 15% |
| Dimethyl sulfoxide | 85% |

The active ingredient is dissolved in dimethyl sulfoxide with mixing and or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

EXAMPLE 2J

A wettable powder is prepared with the composition as follows:

| | |
|---|---|
| Active ingredient | 50% |
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, helminths or protozoa, by spraying or dipping, or by oral administration in drinking water, to control the arthropods, helminths or protozoa.

EXAMPLE 2K

A slow release bolus composition is formed from granules containing the following components in varying Percentages (similar to those described for the previous compositions) depending upon need:

Active ingredient
Density agent
Slow-release agent
Binder

The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods, helminths or protozoa.

EXAMPLE 2L

A slow release composition in the form of granules, pellets, brickettes or the like can be prepared with compositions as follows:

| Active ingredient | 0.5 to 25% |
| Polyvinyl chloride | 75 to 99.5% |
| Dioctyl phthalate | (plasticizer) |

The components are blended and then formed into suitable shapes by melt-extrusion or molding. These composition are useful, for example, for addition to standing water or for fabrication into collars or eartags for attachment to domestic animals to control pests by slow release.

EXAMPLE 2M

A water dispersible granule is prepared with the composition as follows:

| Active ingredient | 85% (max) |
| Polyvinylpyrrolidone | 5% |
| Attapulgite clay | 6% |
| Sodium lauryl sulfate | 2% |
| Glycerine | 2% |

The ingredients are mixed as a 45% slurry with water and wet milled to a particle size of 4 microns, then spray-dried to remove water.

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A method for controlling insects at a locus at which insects are present or are expected to be present, said method comprising applying to said locus an insecticidally effective amount of the compound which is:

3-acetyl-5-amino-1-(2,6-dichloro-4-trifluoromethylphenyl)-4-methylthiopyrazole; or 3-acetyl-5-amino-1-(2,6-dichloro-4-pentafluorothiophenyl)-4-methylthiopyrazole;

or a pesticidally acceptable salt thereof, under conditions in which mammals are exposed to said compound.

2. A method according to claim 1, wherein the compound is 3-acetyl-5-amino-1-(2,6-dichloro-4-trifluoromethylphenyl)-4-methylthiopyrazole or a pesticidally acceptable salt thereof.

3. A method according to claim 1, wherein the insects are sucking insects.

4. A method according to claim 2, wherein the insects are sucking insects.

5. A method according to claim 1, wherein the sucking insects are aphids, plant bugs or stinkbugs.

6. A method according to claim 2, wherein the sucking insects are aphids, plant bugs or stinkbugs.

7. A method according to claim 1, wherein the sucking insects are controlled systemically.

8. A method according to claim 2, wherein the sucking insects are controlled systemically.

9. A method according to claim 1, wherein the locus is an area used or to be used for the growing of crops and the compound is applied at a rate of 5 g to 1 kg per hectare.

10. A method according to claim 2, wherein the locus is an area used or to be used for the growing of crops and the compound is applied at a rate of 5 g to 1 kg per hectare.

11. A method according to claim 1, wherein the locus is an animal and the compound is applied at a rate of 0.1 mg to 20 mg per kg of body weight of animal per day.

12. A method according to claim 2, wherein the locus is an animal and the compound is applied at a rate of 0.1 mg to 20 mg per kg of body weight of animal per day.

13. The compound which is:

3-acetyl-5-amino-1-(2,6-dichloro-4-trifluoromethylphenyl)-4-methylthiopyrazole; or 3-acetyl-5-amino-1-(2,6-dichloro-4-pentafluorothiophenyl)-4-methylthiopyrazole;

or a pesticidally acceptable salt thereof.

14. The compound according to claim 13, which is 3-acetyl-5-amino-1-(2,6-dichloro-4-trifluoromethylphenyl)-4-methylthiopyrazole or a pesticidally acceptable salt thereof.

15. A pesticidal composition comprising a pesticidally effective amount of a compound according to claim 13, or a pesticidally acceptable salt thereof, and a pesticidally acceptable diluent or carrier therefor.

16. A pesticidal composition comprising a pesticidally effective amount of a compound according to claim 14, or a pesticidally acceptable salt thereof, and a pesticidally acceptable diluent or carrier therefor.

17. A process for the preparation of a compound according to claim 13, said process comprising reacting the corresponding 5-amino-3-cyano-1-(2,4,6-trisubstituted phenyl)-4-methylthiopyrazole with a compound of the formula $CH_3M$ wherein M is an alkali metal or an alkaline earth metal salt; followed by, if desired, converting the compound thus obtained into a pesticidally acceptable salt thereof.

18. The process according to claim 17, wherein the compound of the formula $CH_3M$ is methyl magnesium bromide.

* * * * *